United States Patent [19]

Kim et al.

[11] Patent Number: 5,681,790

[45] Date of Patent: Oct. 28, 1997

[54] CATALYST FOR PREPARING METHACRYLIC ACID

[75] Inventors: Young Chul Kim, Kwangjoo; Ki Hwa Lee; Eun Hee Jin, both of Taejeon, all of Rep. of Korea

[73] Assignee: Samsung General Chemicals Co., Ltd., Chungnam, Rep. of Korea

[21] Appl. No.: 565,712

[22] Filed: Nov. 30, 1995

[30] Foreign Application Priority Data

Dec. 26, 1994 [KR] Rep. of Korea .................... 94-36673

[51] Int. Cl.⁶ .................................................. B01J 31/00
[52] U.S. Cl. .......................... 502/164; 502/209; 502/211; 502/311; 502/321; 502/345
[58] Field of Search ............................ 502/321, 164, 502/311, 209, 211, 345; 558/319–324

[56] References Cited

U.S. PATENT DOCUMENTS

| | | | |
|---|---|---|---|
| 4,000,088 | 12/1976 | Shimizu et al. | 252/437 |
| 4,307,247 | 12/1981 | Shaw et al. | 562/509 |
| 4,309,361 | 1/1982 | Suresh et al. | 502/321 |
| 4,413,155 | 11/1983 | Suresh et al. | 502/321 |
| 4,621,155 | 11/1986 | Ueshima et al. | 562/534 |
| 4,710,484 | 12/1987 | Dolhyj et al. | 502/208 |
| 4,843,055 | 6/1989 | Glaeser et al. | 502/202 |
| 5,104,844 | 4/1992 | Yamamoto et al. | 502/200 |
| 5,126,307 | 6/1992 | Yamamoto et al. | 502/200 |

OTHER PUBLICATIONS

Chem. Eng. Technol. 11 (1988) pp. 392–402, Thomas Haeberle et al.: *Kinetic Investigation of Methacrylic Acid Synthesis on Heteropoly–Compounds*.

Applied Catalysis, vol. 4, (1982), pp. 245–256, Mamoru AI: *Effects of Cations Introduced into 12–Molybdophosphoric Acid on the Catalyst Properties*.

Journal of Catalysis, 124 (1990), pp. 247–258, Otto Watzenberger et al.: *Oxydehydrogenation of Isobutyric Acid with heteropolyacid Catalysts: Experimental Observations of Deactivation*.

Stud. Surf. Sci. Catalysis, 7, (1981), pp. 755–767, Shuzo Nakamura et al.: *Vapor Phase Catalytic Oxidation of Isobutene to Methacrylic Acid*.

Chemistry Express, vol. 5, No. 8, (1990), pp. 541–544, Koichi Eguchi et al.: *An Effect of Additives on Catalytic Activity of 12–Molybdophosphoric Acid for Methacrolein Oxidation*, Kinki Chemical Society, Japan.

Primary Examiner—Michael Lewis
Assistant Examiner—Thomas G. Dunn, Jr.
Attorney, Agent, or Firm—Kenyon & Kenyon

[57] ABSTRACT

This invention relates to a novel catalyst for preparing methacrylic acid by gas phase oxidation of methacrolein obtained by gas phase catalytic oxidation of isobutylene or t-butanol. The catalyst is represented by the formula:

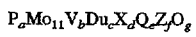

$$P_a Mo_{11} V_b Du_c X_d Q_e Z_f O_g$$

wherein

X is at least one of potassium, rubium, cessium, and thallium;

Z is at least one of lead, antimony, chromium, iron, bismuth, cerium, and zinc;

Q is at least one of organic quaternary ammonium cations consisting of

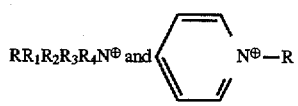

in which

R, $R_1$, $R_2$, $R_3$ and $R_4$ are each independently selected from the group consisting of $C_1$–$C_5$ alkyl or $C_1$–$C_5$ substituted alkyl having functional groups;

a is a number from 0.8 to 1.6;

b is a number from 0.6 to 2;

c is a number from 0.1 to 0.8;

d is a number from 0.7 to 2.2;

e is a number from 0.01 to 0.1;

f is a number from 0 to 0.5; and g is a number of oxygens required to satisfy the valence requirements of the other elements present.

4 Claims, No Drawings

CATALYST FOR PREPARING METHACRYLIC ACID

BACKGROUND OF THE INVENTION

1. Field of the Invention

This invention relates to a novel catalyst for preparing methacrylic acid by gas phase oxidation of methacrolein obtained by gas phase catalytic oxidation of isobutylene or t-butanol.

2. Description of Prior Art

Various kinds of catalysts have been reported as the catalysts for preparing methacrylic acid by gas phase oxidation from methacrolein. Especially, heteropolyacid derivatives have been reported in many patent disclosures as catalysts for preparing methacrylic acid.

However, catalysts comprising heteropolyacid derivatives have drawbacks as solid catalysts owing to their own properties. Therefore, they are not easy to be commercially applied to industry. Furthermore, catalysts comprising heteropolyacid derivatives have poor reproducibility and low mechanical strength as well as a short lifetime. Also, the decline in activity in the presence of impurities consisting of unsaturated hydrocarbons and aromatic compounds has to be improved.

To overcome the drawbacks of heteropolyacid derivative catalysts, many patent disclosures have been published. For example, an arsenic moiety has been added to the catalyst compositions to improve the selectivity. However, it caused a short catalyst lifetime due to the sublimation properties of arsenic.

In Japanese Laying-open Patent Publication No. 82-171, 443, U.S. Pat. No. 4,621,155 and European Patent disclosure 0 454 375 A1, ammonium salts or organic heterocyclic compounds containing nitrogen have been added to the catalyst compositions to improve the selectivity of methacrylic acid. However, they caused a decline in mechanical strength.

To improve the mechanical strength of catalysts, metal sulfate has been tried as an additive in catalyst compositions (Japanese Laying-open Patent Publication No. 80-79,340). However, this catalyst has not shown the good catalytic activity in spite of its good mechanical strength. On the other hand, to improve the catalytic activity, a ceramic whisker, such as, silicon carbide or silicon nitrate has been added to catalyst compositions (Japanese Laying-open Patent Publication No. 84-183,832). This was also difficult; to apply commercially to industry due to the high cost of ceramic whisker.

Generally, methacrolein obtained from the oxidation process of isobutylene or tertiarybutanol contains significant amounts of byproducts such as toluene, acetone, xylene, and other chemicals as well as unconverted isobutylene. Therefore, if the performance of the catalyst declines significantly with the existance of impurities in the methacrolein, it is necessary to employ a methacrolein purification process to minimize the level of impurities in the methacrolein before it is fed into the oxidation process.

From an industrial point of view, however, the addition of a methacrolein purification process is not desirable because of its negative impact on both capital investment and operation costs. Therefore, a need continues to exist to develop a catalyst system which has a high mechanical strength, long life time, and whose performance is not affected by the existance of impurities in methacrolein.

SUMMARY OF THE INVENTION

The object of this invention is to provide a novel catalyst having a high mechanical strength and a long catalyst life, applicable to a process for preparing methacrylic acid from methacrolein at high yield. Another object of this invention is to provide a novel catalyst suitable for a process where methacrolein obtained from an oxidation process of isobutylene or tertiary-butanol can be used without being purified.

The catalyst of this invention has a composition represented by the formula:

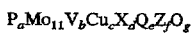

wherein

X is at least one of potassium, rubidium, cesium, and thallium;

Z is at least one of lead, antimony, chromium, iron, bismuth, cerium, and zinc;

Q is at least one organic quaternary ammonium cations consisting of

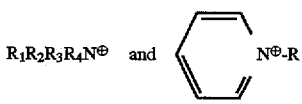

in which

R, $R_1$, $R_2$, $R_3$ and $R_4$ are each independently selected from the group consisting of $C_1$–$C_5$ alkyl or $C_1$–$C_5$ substituted alkyl having functional groups, such as, hydroxy, carboxy, amino and/or oxo;

a is a number from 0.8 to 1.6;

b is a number from 0.6 to 2;

c is a number from 0.1 to 0.8;

d is a number from 0.8 to 2.2;

e is a number from 0.01 to 0.1;

f is a number from 0 to 0.5; and g is the number of oxygens required to satisfy the valence requirements of the other elements present.

DETAILED DESCRIPTION OF THE INVENTION

Among the ingredients of the catalyst composition, phosphorous and molybdenum constitute the main structure of the catalyst. Alkali metals and vanadium are used to improve the selectivity and lifetime of the catalyst.

Copper and Z are used to improve conversion. However, the ingredient represented by Z can be alternatively contained in the catalyst, because ingredient Z is added as the catalyst promoter. In case of absence of ingredient Z, the catalyst composition of this invention can be represented by $P_aMo_{11}V_bCu_cX_dQ_eO_g$.

Adding ingredient Q not only facilitates precipitation of ingredients, but also induces the catalyst to be converted into a properly active structure owing to the properties of the organic quaternary ammonium cartons. Also, among the promoters, the preferred ingredient of X is potassium and preferred ingredients of Z are lead and antimony. Preferred amounts of potassium, lead and antimony are 0.7 to 2.0 of potassium, 0.05 to 0.4 of lead and 0.06 to 0.5 of antimony when molybdenum is 11.

The catalysts of the invention are prepared by the following methods.

Each of the required amounts of phosphomolybdate and vanadium oxide or phosphoric acid, molybdenum oxide and vanadium oxide are dissolved with water. The concentration of the solution is 0.01 to 7M of molybdenum, preferably, 0.02 to 4M of molybdenum. The mixed solution is heated and refluxed for 1 to 20 hours until the color of the solution becomes dark red. After obtaining the red solution, 1 to 8 moles of aqueous solution of ingredient Q per 11 moles of molybdenum in a molar ratio is added to the solution at 0° to 100° C. The promoter ingredients of copper, X and Z can be added to the obtained solution, and the promoter ingredients can be added in the form of nitrates, chlorides, acetates or oxides of the ingredient compounds.

The precipitated catalyst composition is evaporated at 50°–100° C. and dried at 90° to 180° C., preferably, 90°–150° C. The dried catalyst is crushed and passed through a 60 mesh sieve.

Finally, the obtained catalyst particles are formed by the methods of tableting, extruding, heeding or coating. The formed catalyst is calcined at 300° to 420° C. for 1 to 10 hours in an oxygen/nitrogen atmosphere having 0.1 to 20% of oxygen, preferably, 0.1 to 15% of oxygen. During the calcination step, it is important to increase the temperature gradually; a suitable temperature-increase rate is 0.1° to 10° C./min, preferably, 0.2° to 5° C./min.

The activity and selectivity of the obtained catalysts are measured by tests disclosed in the following example. However, the scope of the invention is not limited by these examples.

EXAMPLE 1

300 g of molybdenum trioxide, 17.2 g of vanadium pentoxide and 26.1 g of 85% phosphoric acid were dissolved with 1500 ml of water in round bottom flask and refluxed with stirring for 5 hours. The obtained red solution was called solution A.

79.2 g of choline chloride ($C_4H_{14}ClNO$), 28.6 g of potassium nitrate and 13.7 g of cupric nitrate trihydrate were dissolved with 500 ml of water in 1000 ml beaker. The obtained solution was called solution B.

Solution A and solution B were mixed and vigorously stirred in 3000 ml beaker. After obtaining a yellow precipitate, the mixture was further aged at 70° C. for 5 hours. After evaporating, the obtained slurry was dried in an electric furnace at 110° C.

The obtained dried cluster was crushed and screened with a 60 mesh sieve. Then, 1% starch solution was added to the obtained catalyst powder in the kneader to make a paste. Using the extruder, the catalyst paste was extruded and pelletized to obtain pellets 6 mm in diameter and 5 mm in length. Finally, the formed catalyst was calcined at 220° C. for one hour and at 360° C. for 5 hours in a oxygen/nitrogen atmosphere having 5% oxygen. For this calcination, the temperature of calcination is gradually increased at a rate of 0.5° C./min.

The obtained catalyst composition was crushed for testing. The composition of catalyst was $P_{1.2}Mo_{11}V_1Cu_{0.3}Q_xK_{1.5}$, wherein Q was choline and x was 0.08. The value of x can be varied according to the calcination condition.

The tests for measuring the properties of the obtained catalyst were conducted under the following conditions. A mixed gas obtained from the gas phase oxidation of isobutylene was used as a starting material for this reaction. The composition of the mixed gas was 3.8% of methacrolein, 0.2% of isobutylene, 0.12% of methacrylic acid, 0.07% of acetone, 0.3% of $CO_2$, 0.03% CO, 9.8% of oxygen, 15% of steam, 0.04% of impurities including toluene, xylene, formaldehyde, acetic acid, acrolein and aromatic compounds and others balance of nitrogen. The reacted products were measured by gas chromatography and the mechanical strength of the catalyst was measured by a grain crushing strength tester made by Geo Mechanic Co.

The reaction conditions, reaction results and mechanical strength of the catalyst are reported in Table 1.

EXAMPLE 2

The catalyst was prepared by the same manner of example 1, except that 66.4 g of betaine ($C_5H_{11}NO_2$) was used instead of choline chloride. The obtained catalyst composition was $P_{1.2}Mo_{11}V_1Cu_{0.3}Q_{0.08}K_{1.5}$, wherein Q was betaine. The reaction conditions, reaction results and mechanical strength of the catalyst are reported in Table 1.

EXAMPLE 3

The catalyst was prepared by the same manner of example 1, except that 125.3 g of N-methyl pyridium iodide ($C_6H_8IN$) was used instead of choline chloride. The composition of obtained catalyst was $P_{1.2}Mo_{11}V_1Cu_{0.3}Q_{0.02}K_{1.5}$, wherein Q was N-methyl pyridium. The reaction conditions, reaction results and mechanical strength of the catalyst are reported in Table 1.

EXAMPLE 4

The catalyst was prepared by the same manner of example 1, except that 106.6 g of N-ethyl pyridium bromide ($C_7H_{10}BrN$) was used instead of choline chloride. The composition of obtained catalyst was $P_{1.2}Mo_{11}V_1Cu_{0.3}K_{1.5}$, wherein Q was N-ethyl pyridium. The reaction conditions, reaction results and mechanical strength of the catalyst are reported in Table 1.

EXAMPLE 5

The catalyst was prepared by the same manner of example 1, except that 114.5 g of N-propyl pyridium bromide ($C_8H_{12}BrN$) was used instead of choline chloride. The composition of obtained catalyst was $P_{1.2}Mo_{11}V_1Cu_{0.3}Q_{0.08}K_{1.5}$, wherein Q was N-propyl pyridium. The reaction conditions, reaction results and mechanical strength of the catalyst are reported in Table 1.

EXAMPLE 6

The catalyst was prepared by the same manner of example 1, except that 62.1 g of tetra methyl ammonium chloride ($C_4H_{12}ClN$) was used instead of choline chloride. The composition of obtained catalyst was $P_{1.2}Mo_{11}V_1Cu_{0.3}Q_{0.08}K_{1.5}$, wherein Q was tetra methyl ammonium. The reaction conditions, reaction results and mechanical strength of the catalyst are reported in Table 1.

EXAMPLE 7

The catalyst was prepared by the same manner of example 1, except that 157.3 g of tetra buthyl ammonium chloride ($C_{16}H_{36}ClN$) was used instead of choline chloride. The composition of obtained catalyst was $P_{1.2}Mo_{11}V_1Cu_{0.3}Q_{0.08}K_{1.5}$, wherein Q was tetra buthyl ammonium. The reaction conditions, reaction results and mechanical strength of the catalyst are reported in Table 1.

EXAMPLE 8

The catalyst was prepared by the same manner of example 1, except that 12.5 g of lead nitrate was added to solution B.

The composition of obtained catalyst was $P_{1.2}Mo_{11}V_1Cu_{0.3}Q_{0.08}K_{1.5}b_{0.2}$, wherein Q was choline. The reaction conditions, reaction results and mechanical strength of the catalyst are reported in Table 1.

EXAMPLE 9

The catalyst was prepared by the same manner of example 1, except that 9.17 g of antimony pentoxide was added to solution A. The composition of obtained catalyst was $P_{1.2}Mo_{11}V_1Cu_{0.3}Q_{0.08}K_{1.5}Sb_{0.3}$, wherein Q was choline. The reaction conditions, reaction results and mechanical strength of the catalyst are reported in Table 1.

EXAMPLE 10

The catalyst was prepared by the same manner of example 9, except that 12.5 g of lead nitrate was added to solution B. The composition of obtained catalyst was $P_{1.2}Mo_{11}V_1Cu_{0.3}Q_{0.08}K_{1.5}Sb_{0.3}Pb_{0.2}$, wherein Q was choline. The reaction conditions, reaction results and mechanical strength of the catalyst are reported in Table 1.

EXAMPLE 11

The catalyst was prepared by the same manner of example 1, except that 1.89 g of chromium trioxide was added to solution A. The composition of obtained catalyst was $P_{1.2}Mo_{11}V_1Cu_{0.3}Q_{0.08}K_{1.5}Cr_{0.1}$, wherein Q was choline. The reaction conditions, reaction results and mechanical strength of the catalyst are reported in Table 1.

EXAMPLE 12

The catalyst was prepared by the same manner of example 1, except that 6.61 g of ferric nitrate hexahydrate was added to solution B. The composition of obtained catalyst was $P_{1.2}Mo_{11}V_1Cu_{0.3}Q_{0.08}K_{1.5}Fe_{0.1}$, wherein Q was choline. The reaction conditions, reaction results and mechanical strength of the catalyst are reported in Table 1.

EXAMPLE 13

The catalyst was prepared by the same manner of example 1, except that 9.17 g of bismuth nitrate pentahydrate was added to solution B. The composition of obtained catalyst was $P_{1.2}Mo_{11}V_1Cu_{0.3}Q_{0.08}K_{1.5}Bi_{0.1}$, wherein Q was choline. The reaction conditions, reaction results and mechanical strength of catalyst were reported in Table 1.

EXAMPLE 14

The catalyst was prepared by the same manner of example 1, except that 16.41 g of cesium nitrate hexahydrate was added to solution B. The composition of obtained catalyst was $P_{1.2}Mo_{11}V_1Cu_{0.3}Q_{0.08}K_{1.5}Ce_{0.1}$, wherein Q was choline. The reaction conditions, reaction results and mechanical strength of the catalyst are reported in Table 1.

EXAMPLE 15

The catalyst was prepared by the same manner of example 1, except that 9.20 g of zinc nitrate was added to solution B. The composition of obtained catalyst was $P_{1.2}Mo_{11}V_1Cu_{0.3}Q_{0.08}K_{1.5}Zn_{0.2}$, wherein Q was choline. The reaction conditions, reaction results and mechanical strength of the catalyst are reported in Table 1.

EXAMPLE 16

The catalyst was prepared by the same manner of example 1, except that 47.89 g of cesium nitrate was added to solution B instead of potassium nitrate. The composition of obtained catalyst was $P_{1.2}Mo_{11}V_1Cu_{0.3}Q_{0.08}Cs_{1.3}$, wherein Q was choline. The reaction conditions, reaction results and mechanical strength of the catalyst are reported in Table 1.

COMPARATIVE EXAMPLE 1

The catalyst was prepared by the same manner of example 10, except that choline chloride was not added in solution B. The composition of obtained catalyst was $P_{1.2}Mo_{11}V_1Cu_{0.3}K_{1.5}Sb_{0.3}Pb_{0.2}$. The reaction conditions, reaction results and mechanical strength of the catalyst are reported in Table 2.

COMPARATIVE EXAMPLE 2

The catalyst was prepared by the same manner of example 10, except that 30.32 g of ammonium chloride was added in solution B instead of choline chloride. The composition of obtained catalyst was $P_{1.2}Mo_{11}V_1Cu_{0.3}(NH_4)_{0.3}K_{1.5}Sb_{0.3}Pb_{0.2}$. The reaction conditions, reaction results and mechanical strength of the catalyst are reported in Table 2.

COMPARATIVE EXAMPLE 3

The catalyst was prepared by the same manner of example 10, except that 44.85 g of pyridine was added in solution B instead of choline chloride. The composition of obtained catalyst was $P_{1.2}Mo_{11}V_1Cu_{0.3}(C_5H_5N)_{0.1}K_{1.5}Sb_{0.3}Pb_{0.2}$. The reaction conditions, reaction results and mechanical strength of the catalyst are reported in Table 2.

TABLE 1

The reaction conditions, reaction results and mechanical strength of the catalysts

| No. of Example | Reaction Temperature (°C.) | Contact Time (sec) | Conversion of Methacrolein (%) | Selectivity of Methacrylic Acid (%) | Grain crushing strength (kg/cm) |
|---|---|---|---|---|---|
| 1 | 290 | 3.0 | 88.3 | 87.6 | 3.2 |
| 2 | 290 | 3.0 | 90.7 | 85.3 | 3.5 |
| 3 | 310 | 3.0 | 88.7 | 88.5 | 2.0 |
| 4 | 310 | 3.0 | 85.4 | 88.2 | 1.6 |
| 5 | 310 | 3.0 | 85.7 | 87.3 | 1.5 |
| 6 | 300 | 3.0 | 89.0 | 81.2 | 2.7 |
| 7 | 300 | 3.0 | 87.9 | 82.7 | 2.1 |
| 8 | 290 | 3.0 | 88.1 | 88.3 | 3.2 |
| 9 | 290 | 3.0 | 88.5 | 88.1 | 3.3 |
| 10 | 290 | 3.0 | 88.5 | 89.6 | 3.3 |
| 11 | 280 | 3.0 | 90.7 | 84.2 | 3.2 |
| 12 | 280 | 3.0 | 85.4 | 86.3 | 3.1 |
| 13 | 280 | 3.0 | 87.7 | 87.1 | 3.3 |
| 14 | 290 | 3.0 | 88.5 | 88.1 | 3.2 |
| 15 | 300 | 3.0 | 86.4 | 87.3 | 3.0 |
| 16 | 300 | 3.0 | 90.4 | 88.6 | 2.9 |

TABLE 2

The reaction conditions, reaction results and mechanical strength the of catalysts

| No. of Comparative Example | Reaction Temperature (°C.) | Contact Time (sec) | Conversion of Methacrolein (%) | Selectivity of Methacrylic Acid (%) | Grain crushing strength (kg/cm) |
|---|---|---|---|---|---|
| 1 | 320 | 3.0 | 85.8 | 77.6 | 0.1 |
| 2 | 320 | 3.0 | 89.6 | 82.4 | 0.9 |
| 3 | 320 | 3.0 | 87.6 | 84.7 | 0.8 |

We claim:

1. A catalyst composition for preparing methacrylic acid by gas phase oxidation of methacrolein having impurities, said catalyst having a high mechanical strength and a long catalyst life represented by the formula:

$$P_aMo_{11}V_bCu_cX_dQ_eZ_fO_g$$

wherein

X is at least one of potassium, rubium, cessium, and thallium;

Z is at least one of lead, antimony, chromium, iron, bismuth, cerium, and zinc;

Q is at least one of organic quaternary ammonium cations consisting of

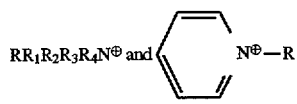

in which

R, $R_1$, $R_2$, $R_3$ and $R_4$ are each independently selected from the group consisting of $C_1$–$C_5$ alkyl or $C_1$–$C_5$ substituted alkyl having functional groups;

a is a number from 0.8 to 1.6;

b is a number from 0.6 to 2;

c is a number from 0.1 to 0.8;

d is a number from 0.7 to 2.2;

e is a number from 0.01 to 0.1;

f is a number from 0 to 0.5; and g is a number of oxygens required to satisfy the valence requirements of the other elements present.

2. The catalyst composition for preparing methacrylic acid according to claim 1, wherein X is potassium and Z is one or more lead and antimony.

3. The catalyst composition for preparing methacrylic acid according to claim 2, wherein d is 0.7 to 2.0, f is 0.05 to 0.4 when Z is lead and f is 0.06 to 0.5 when z is antimony.

4. A process for producing the catalyst composition represented by the formula of claim 1 comprising the steps of:

i) dissolving each required amount of phosphomolybdate and vanadium oxide or each required amount of phosphoric acid, molybdenum oxide and vanadium oxide in water to form a mixed solution;

ii) heating and refluxing the mixed solution for 1 to 20 hours;

iii) adding 1 to 8 moles of an aqueous solution of Q per 11 moles of molybdenum in a molar ratio;

iv) adding copper, X and Z to obtain a mixture;

v) evaporating and drying the mixture to obtain a dried composition; and vi) forming and calcining the dried composition.

* * * * *

UNITED STATES PATENT AND TRADEMARK OFFICE
CERTIFICATE OF CORRECTION

PATENT NO. : 5,681,790
DATED : 28 October 1997          Page 1 of 2
INVENTOR(S) : Young Chul KIM et al.

It is certified that error appears in the above-identified patent and that said Letters Patent is hereby corrected as shown below:

In the Abstract, line 5: Change "$P_aM_0V_bDu_cX_dQ_eZ_fO_g$" to --$P_aM_0V_bCu_cX_dQ_eZ_fO_g$--.

| Column | Line | |
|---|---|---|
| 1 | 40 | After "shown" delete "the". |
| 1 | 45 | After "difficult" delete ";". |
| 2 | 17 | Change "cations" to --cation--. |
| 2 | 57 | Change "cartons" to --cations--. |
| 3 | 13 | After "catalyst" insert --composition--. |
| 3 | 16 | Change "heeding" to --beeding-- |
| 3 | 32 | Before "round" insert --a--. |

UNITED STATES PATENT AND TRADEMARK OFFICE
CERTIFICATE OF CORRECTION

PATENT NO. : 5,681,790
DATED : 28 October 1997
INVENTOR(S) : Young Chul KIM et al.

It is certified that error appears in the above-identified patent and that said Letters Patent is hereby corrected as shown below:

| Column | Line | |
|---|---|---|
| 3 | 50 | Change "in a" to --in an--. |
| 4 | 42 | Change "$Q_{0.08}$" to --$Q_{0.03}$--. |
| 5 | 2 | Change "$b_{0.2}$" to --$Pb_{0.2}$--. |
| 5 | 46 | Change "of catalyst were" to --of the catalyst are--. |
| 6 | 58 | Change "the of catalysts" to --of the catalysts--. |
| 8 | 9 | Before "lead" insert --of--. |
| 8 | 12 | Change "z" to --Z--. |

Signed and Sealed this

Eighth Day of September, 1998

Attest:

BRUCE LEHMAN

Attesting Officer      Commissioner of Patents and Trademarks